United States Patent
Chambard et al.

(10) Patent No.: US 7,053,027 B2
(45) Date of Patent: May 30, 2006

(54) LUBRICATING OIL COMPOSITIONS

(75) Inventors: Laurent Chambard, Oxfordshire (GB); Terence Garner, Oxon (GB)

(73) Assignee: Infineum International Limited (GB)

( * ) Notice: Subject to any disclaimer, the term of this patent is extended or adjusted under 35 U.S.C. 154(b) by 66 days.

(21) Appl. No.: 09/846,483

(22) Filed: May 1, 2001

(65) Prior Publication Data

US 2002/0082176 A1 Jun. 27, 2002

(30) Foreign Application Priority Data

May 9, 2000 (GB) .................................. 0011115.3

(51) Int. Cl.
*C10M 159/20* (2006.01)

(52) U.S. Cl. ...................................... 508/460; 508/378

(58) Field of Classification Search ................ 508/518, 508/371, 378, 460
See application file for complete search history.

(56) References Cited

U.S. PATENT DOCUMENTS

| | | | | |
|---|---|---|---|---|
| 3,625,893 A | * | 12/1971 | Brook et al. ................ | 508/378 |
| 4,283,294 A | * | 8/1981 | Clarke ........................ | 508/378 |
| 5,558,802 A | * | 9/1996 | Dowling .................... | 508/391 |
| 5,672,570 A | | 9/1997 | Miyaji et al. ............... | 508/192 |
| 5,672,572 A | * | 9/1997 | Arai et al. .................. | 508/364 |
| 6,103,672 A | * | 8/2000 | Dunn et al. ................. | 508/185 |
| 6,114,288 A | * | 9/2000 | Fujitsu et al. .............. | 508/371 |
| 6,140,280 A | * | 10/2000 | Nakano et al. ............. | 508/291 |
| 6,140,281 A | * | 10/2000 | Blahey et al. .............. | 508/398 |
| 6,140,282 A | * | 10/2000 | Cartwright et al. ......... | 508/398 |
| 6,147,035 A | * | 11/2000 | Sougawa et al. ........... | 508/192 |
| 6,153,565 A | * | 11/2000 | Skinner et al. ............. | 508/391 |
| 6,281,179 B1 | * | 8/2001 | Skinner et al. ............. | 510/184 |
| 6,329,328 B1 | * | 12/2001 | Koganei et al. ............ | 508/365 |

FOREIGN PATENT DOCUMENTS

| | | |
|---|---|---|
| WO | WO89/04358 A2 | 5/1989 |
| WO | WO96/20265 | 7/1996 |
| WO | WO96/37582 | 11/1996 |
| WO | WO00/63325 | 10/2000 |

* cited by examiner

*Primary Examiner*—Ellen M. McAvoy

(57) ABSTRACT

A trunk piston marine diesel engine lubricating oil composition is dispersant-free, has a TBN of 25 or greater, and comprises
(A) an oil of lubricating viscosity,
(B) an aromatic carboxylate as the sole overbased metal detergent, and
(C) an antiwear additive.

14 Claims, No Drawings

LUBRICATING OIL COMPOSITIONS

This invention relates to a trunk piston marine engine lubricating composition for a medium speed 4-stroke compression-ignited (diesel) marine engine and lubrication of such a trunk piston engine.

The term "marine" does not restrict the engines to those used in water-borne vessels; as is understood in the art, it also includes those for auxiliary power generation applications and for main propulsion stationary land-based engines of the above types for power-generation.

One problem associated with trunk piston engines is that their manufacturers commonly design them to use a variety of diesel fuels, ranging from good quality high distillate fuel with low sulfur and low asphaltene content to poorer quality intermediate or heavy fuel such as "Bunker W or residual fuel oil with generally higher sulfur and higher asphaltene content. Lubricants used in such engines often become contaminated with asphaltene components from the fuel, leading to cleanliness problems in service, sometimes referred to as "black paint".

Lubricating oils compositions (or lubricants) for trunk piston engines are known and may be referred to as trunk piston engine oils or TPEO's. They are known to include, as additives to improve their performance, ashless dispersants and overbased detergents.

EP-A-0-662 508 meets the above problem by describing use of a composition that includes a hydrocarbyl-substituted phenate concentrate having a TBN greater than 300, and at least one of a hydrocarbyl-substituted salicylate and a hydrocarbyl-substituted sulphonate. However, the composition also includes, apparently, a dispersant since the EP states that lubricating oils for medium speed diesel engines typically comprise dispersants to minimise deposit formation in various parts of the engine.

Thus, EP-A-0-662 508 requires several additives to meet the problem, thus increasing cost in a cost-sensitive environment.

It has now surprisingly been found that a dispersant-free TPEO, wherein the overbased metal detergent is of the aromatic carboxylate, such as salicylate, type only, provides excellent performance in several respects, i.e. without the need for certain additional additives as required by the prior art, for example any other overbased metal detergents, such as overbased phenates or overbased sulfonates.

Accordingly, a first aspect of the present invention is a trunk piston marine engine lubricating oil composition for a medium speed compression-ignited (diesel) marine engine wherein the composition is dispersant-free and has a Total Base Number (TBN) of 25 or greater, and comprises:
- (A) an oil of lubricating viscosity, in a major amount, and added thereto:
- (B) an oil-soluble overbased metal detergent additive, as the sole overbased metal detergent, consisting of one or more aromatic carboxylates, in a minor amount, and
- (C) an antiwear additive, in a minor amount.

A second aspect of the present invention is trunk piston marine engine lubricating oil composition for a medium speed compression-ignited (diesel) marine engine wherein the composition is dispersant-free and has a Total Base Number (TBN) of 25 or greater, and comprises:
- (A) an oil of lubricating viscosity, in a major amount, and added thereto:
- (B) an oil-soluble overbased metal detergent additive consisting of, as the sole metal detergent, one or more hydrocarbyl-substituted salicylates, in a minor amount, and
- (C) an antiwear additive comprising a dihydrocarbyl dithiophosphate metal salt, in a minor amount.

A third aspect of the present invention is the use of additives (B) and (C) as defined in the first or second aspect of the invention in a dispersant-free trunk piston marine engine oil lubricating composition having a TBN of 25 or greater to (a) suspend asphaltene components in the composition, or (b) control piston deposits, or both (a) and (b), when used in a medium speed compression-ignited marine engine.

A fourth aspect of the present invention is a method of lubricating a medium speed compression-ignited marine engine which comprises supplying to the engine the trunk piston marine engine oil lubricating composition according to the first or second aspect of the invention.

"Major amount" means in excess of 50 mass % of the composition.

"Minor amount" means less than 50 mass % of the composition, both in respect of the stated additive and in respect of the total mass % of all the additives present in composition, reckoned as active ingredient of the additive or additives.

"Comprises or comprising" or cognate words is taken to specify the presence of stated features, steps, integers or components, but does not preclude the presence or addition of one or more other features, steps, integer components or groups thereof.

"TBN" (Total Base Number) is as measured by ASTM D2896, and the viscosity index is as defined by ASTM D2270.

The features of the invention will now be discussed in more detail below.

Marine Diesel Engines

The lubricating oil composition of the present invention may be suitable for use in a 4-stroke trunk piston engine having an engine speed of 200 to 2,000 e.g. 400 to 1,000, rpm, and a brake horse-power (BHP) per cylinder of 50 to 3,000, preferably 100 to 2,000.

Lubricating Oil Composition

Preferably, the TBN of the lubricant composition is in the range of from 25 to 100, such as from 25 or 30 to 60, preferably 40 to 55.

Preferably, the viscosity index of the lubricant composition is at least 90, more preferably at least 95, and at most 140 such as 120, preferably 110. A preferred viscosity index range is from 95 to 115.

The lubricant composition may, for example, have a kinematic viscosity at 100° C. (as measured by ASTM D445) of at least 9, preferably at least 13, more preferably in the range of from 14 to 24, for example from 14 to 22, $mm^2s^{-1}$.

(A) Oil of Lubricating Viscosity

The oil of lubricating viscosity (sometimes referred to as lubricating oil) may be any oil suitable for the lubrication of a trunk piston engine. The lubricating oil may suitably be an animal, a vegetable or a mineral oil. Suitably the lubricating oil is a petroleum-derived lubricating oil, such as a naphthenic base, paraffinic base or mixed base oil. Alternatively, the lubricating oil may be a synthetic lubricating oil. Suitable synthetic lubricating oils include synthetic ester lubricating oils, which oils include diesters such as di-octyl adipate, di-octyl sebacate and tridecyl adipate, or polymeric hydrocarbon lubricating oils, for example liquid polyisobutene and poly-alpha olefins.

Commonly, a mineral oil is employed. The lubricating oil may generally comprise greater than 60, typically greater than 70, mass % of the composition, and typically have a kinematic viscosity at 100° C. of from 2 to 40, for example from 3 to 15, $mm^2s^{-1}$ and a viscosity index of from 80 to 100, for example from 90 to 95.

Another class of lubricating oils is hydrocracked oils, where the refining process further breaks down the middle and heavy distillate fractions in the presence of hydrogen at high temperatures and moderate pressures. Hydrocracked oils typically have a kinematic viscosity at 100° C. of from 2 to 40, for example from 3 to 15, $mm^2s^{-1}$ and a viscosity index typically in the range of from 100 to 110, for example from 105 to 108.

The lubricating compositions of the present invention are free of dispersants in the sense of containing substantially no dispersant. The lubricating composition in every aspect of the present invention may, however, contain small amounts of a dispersant, provided the composition does not substantially demonstrate the dispersancy effect of the component.

A dispersant is an additive for a lubricating composition whose primary function is to hold solid and liquid contaminants in suspension, thereby passivating them and reducing engine deposits at the same time as reducing sludge depositions. Thus, for example, a dispersant maintains in suspension oil insoluble substances that result from oxidation during use of the lubricating oil, thus preventing sludge flocculation and precipitation or deposition on metal parts of the engine.

A noteworthy class of dispersants are "ashless", meaning a non-metallic organic material that forms substantially no ash on combustion, in contrast to metal containing, hence ash-forming, materials. Ashless dispersants comprise a long chain hydrocarbon with a polar head, the polarity being derived from inclusion of, e.g. an O, P or N atom. The hydrocarbon is an oleophilic group that confers oil solubility, having for example 40 to 500 carbon atoms.

Thus, ashless dispersants may comprise an oil-soluble polymeric hydrocarbon backbone having functional groups that are capable of associating with particles to be dispersed.

(B) Overbased Metal Detergent

A detergent is an additive that reduces formation of piston deposits, for example high-temperature varnish and lacquer deposits, in engines; it has acid-neutralising properties and is capable of keeping finely divided solids in suspension. It is based on metal "soaps", that is metal salts of acidic organic compounds, sometimes referred to as surfactants, which, in the present case, is an aromatic carboxylic acid only, such as salicylic acid.

The aromatic moiety of the aromatic carboxylic acid can contain heteroatoms, such as nitrogen. Preferably, the moiety contains only carbons atoms. The moiety may contain at least 4 carbon atoms, preferably six or more carbon atoms; for example benzene is a preferred moiety.

The aromatic carboxylic acid surfactant may contain one or more aromatic moieties, such as one or more benzene rings, either fused or connected via alkylene bridges.

Preferably the carboxylic acid group is attached directly to a carbon atom on the aromatic moiety, such as on the benzene ring.

More preferably, the aromatic moiety also contains a second functional group, such as a hydroxy group or a sulfonate group, which can be attached directly or indirectly to a carbon atom on the aromatic moiety.

The detergent comprises a polar head with a long hydrophobic tail; the polar head comprises a metal salt of the aromatic carboxylic acid, such as salicylic acid. Large amounts of a metal base are included by reacting an excess of a metal compound, such as an oxide or hydroxide, with an acidic gas such as carbon dioxide to give an overbased detergent which comprises a neutralised detergent, such as a metal salt of a surfactant and a metal base (e.g. carbonate) micelle.

The overbased detergents of this invention may have a TBN in the range of 60 to 600, preferably 100 to 450, more preferably 160 to 400.

The metal may be an alkali or alkaline earth metal, e.g., sodium, potassium, lithium, calcium, and magnesium. Calcium is preferred.

Surfactants for the surfactant system of the overbased metal detergents can contain at least one hydrocarbyl group, for example, as a substituent on an aromatic ring. Preferably the aromatic carboxylic acids effective in the present invention have a hydrocarbyl group attached directly to a carbon atom on the aromatic moiety.

The term "hydrocarbyl" as used herein means that the group concerned is primarily composed of hydrogen and carbon atoms and is bonded to the remainder of the molecule via a carbon atom, but does not exclude the presence of other atoms or groups in a proportion insufficient to detract from the substantially hydrocarbon characteristics of the group. Advantageously, hydrocarbyl groups in surfactants for use in accordance with the invention are aliphatic groups, preferably alkyl or alkylene groups, especially alkyl groups, which may be linear or branched. The total number of carbon atoms in the surfactants should be at least sufficient to impact the desired oil-solubility.

The hydrocarbyl group may contain contain 5 to 100, preferably 9 to 30, especially 14 to 20, carbon atoms.

Aromatic carboxylates, preferably salicylates, used in accordance with the invention may be non-sulfurized or sulfurized, and may be chemically modified and/or contain additional substitutents. Process for sulfurizing, for example a hydrocarbyl-substituted salicylic acid, are well known to those skilled in the art.

Salicylic acids are typically prepared by the carboxylation, by the Kolbe-Schmitt process, of phenoxides, and in that case, will generally be obtained, normally in a diluent, in admixture with uncarboxylated phenol.

Preferred substituents in oil-soluble salicylic acids from which salicylates in accordance with the invention may be derived are alkyl substituents. In alkyl-substituted salicylic acids, the alkyl groups advantageously contain 5 to 100, preferably 9 to 30, especially 14 to 20, carbon atoms. Where there are more than one alkyl groups, the average number of carbon atoms in all of the alkyl groups is preferably at least 9 to ensure adequate oil-solubility.

The aromatic carboxylates, such as salicylates, may be used in a proportion in the range of 0.5 to 30, preferably 2.5 to 15 or to 20, mass % based on the mass of the lubricating oil composition.

A preferred overbased metal detergent is a calcium salicylate.

(C) Antiwear Additive

This reduces friction and excessive wear and is usually based on compounds containing sulfur or phosphorus or both, for example that are capable of depositing polysulfide films on the surfaces involved. Noteworthy are dihydrocarbyl dithiophosphate metal salts, which constitute preferred anti-wear additives in the present invention.

The metal in the dihydrocarbyl dithiophosphate metal may be an alkali or alkaline earth metal, or aluminium, lead, tin, molybdenum, manganese, nickel or copper.

Zinc salts are preferred as the antiwear additive.

Preferably the antiwear additive, such as the metal dihydrocarbyl dithiophosphate salt, is present in the range of 0.1 to 1.5, preferably 0.5 to 1.3, mass %, based upon the total mass of the lubricating oil composition.

The metal dihydrocarbyl dithiophosphate salts may be prepared in accordance with known techniques by first forming a dihydrocarbyl dithiophosphoric acid (DDPA), usually by reaction of one or more alcohol or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared comprising both hydrocarbyl groups that are entirely secondary in character and hydrocarbyl groups that are entirely primary in character. To make the zinc salt, any basic or neutral zinc compound may be used but the oxides, hydroxides and carbonates are most generally employed. Commercial additives frequently contain an excess of zinc due to use of an excess of the basic zinc compound in the neutralisation reaction.

The preferred zinc dihydrocarbyl dithiophosphates are oil-soluble salts of dihydrocarbyl dithiophosphoric acids and may be represented by the following formula:

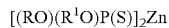

$[(RO)(R^1O)P(S)]_2Zn$ where R and $R^1$ may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylehexyl, phenyl, butylphenyl, cyclohexyl, methylcyclopentyl, propenyl, butenyl. In order to obtain oil-solubility, the total number of carbon atoms (i.e. in R and $R^1$) in the dithiophosphoric acid will generally be 5 or greater. The zinc dihydrocarbyl dithiophosphate can therefore comprise zinc dialkyl dithiophosphates.

Examples of ashless, i.e. non metal-containing, anti-wear agents include 1,2,3-trizoles, benzotriazoles, thiadiazoles, sulfurised fatty acid esters, and dithiocarbamate derivatives.

Other additives such as pour point depressants, antifoamants, and/or demulsifiers may be provided, if necessary.

It may be desirable, although not essential, to prepare one or more additive packages or concentrates comprising the additives, whereby additives (B) and (C) can be added simultaneously to the base oil to form the lubricating oil composition. Dissolution of the additive package(s) into the lubricating oil may be facilitated by solvents and by mixing accompanied with mild heating, but this is not essential. The additive package(s) will typically be formulated to contain the additive(s) in proper amounts to provide the desired concentration, and/or to carry out the intended function in the final formulation when the additive package(s) is/are combined with a predetermined amount of base lubricant. Thus, additives (B) and (C), in accordance with the present invention, may be admixed with small amounts of base oil or other compatible solvents together with other desirable additives to form additive packages containing active ingredients in an amount, based on the additive package, of, for example, from 2.5 to 90, preferably from 5 to 75, most preferably from 8 to 60, mass % of additives in the appropriate proportions, the remainder being base oil.

The final formulations may typically contain about 5 to 40 mass % of the additive packages(s), the remainder being base oil.

The term 'active ingredient' (a.i.) as used herein refers to the additive material that is not diluent.

The terms 'oil-soluble' or 'oil-dispersable' as used herein do not necessarily indicate that the compounds or additives are soluble, dissolvable, miscible or capable of being suspended in the oil in all proportions. These do mean, however, that they are, for instance, soluble or stably dispersible in oil to an extent sufficient to exert their intended effect in the environment in which the oil is employed. Moreover, the additional incorporation of other additives may also permit incorporation of higher levels of a particular additive, if desired.

The lubricant compositions of this invention comprise defined individual (i.e. separate) components that may or may not remain the same chemically before and after mixing.

EXAMPLES

The present inventions is illustrated by, but in no way limited to, the following examples.

Components

The components used in the examples were as follows.

Overbased Metal Detergents:

B1—an overbased calcium salicylate having a TIBN of 168, after dilution.

B2—an overbased calcium salicylate having a TBN of 280, after dilution.

Anti-wear Additives

C1—a zinc dialkyldithiophosphate (ZDDP) made from a primary C8 alcohol.

Other Components

T—antifoamant

Lubricant Compositions and Tests

Lubricant compositions as trunk piston marine diesel lubricating oils were prepared by admixing with a basestock the components B1 and B2 and component C1, and optionally component T, as identified above. The admixing was carried out by blending at elevated temperature. Two compositions were prepared to have the following formulations:

| Component | Oil 1 | Oil 2 |
| --- | --- | --- |
| B1 | 10.10 | 12.50 |
| B2 | 5.65 | 6.84 |
| C1 | 0.61 | 0.61 |
| T | 10 ppm | — |
| Base Oil | Balance | Balance |
| TBN | 30 | 40 |

Unless otherwise stated, the figures above represent mass % values, based on the mass of the composition.

Oil 1 and Oil 2, being compositions of the invention, were tested as described below, as were the following comparison compositions, being at some stage commercially available.

Reference Oil 1: has a TBN of 30; comprises, as overbased detergent, a combination of calcium phenate and calcium sulfonate; as antiwear additive, a zinc dialkyldithiophosphate; and a polyalkenyl-substituted succinimide dispersant.

Reference Oil 2: as Reference Oil 1 but having, as overbased detergent, a combination of calcium phenate, calcium salicylate and calcium sulfonate.

Reference Oil 3: as Reference Oil 1 having a TBN of 40.

Each of the above-described compositions was tested by using them to lubricate a Wartsila 4L20 trunk piston power generation 4-stroke, heavy fuelled, diesel engine for 500 hours. At the beginning of each test, engine components were clean and within the manufacturer's specification. At the end of each test, the pistons (4) were removed and examined as follows:

Rating (i) visually for ring grooves fillings to provide a percentage of the uppermost groove (Groove 1) and the next lower groove (Groove 2) that is filled with deposit;

Rating (ii) visually for overall piston rating expressed as a weighted demerit according to the Caterpillar 1-K method; and Rating (iii) measuring the amount of deposit, expressed as its depth in microns as an area-weighted average, on the walls of the oil-cooling gallery (sometimes referred to as "undercrown , or UC, deposits").

Rating (i) and rating (ii) were performed according to the CRC rating procedure described in the CRC Manual No. 18 (1991), and rating (iii) was performed as described in the Wartsila-NSD procedure 'The Limits for Deposit Thicknesses and Component Wear in Connection with Lubricating Oil Approval Tests, MSLWD2.DOC (1st Feb. 1999)'. The results of rating (iii) provide an indication of the ability of the composition to combat the "black paint" problem referred to hereinbefore.

Results

The results of the above tests, reported as an average over the 4 cylinders, are summarised below:

| COMPOSITIONS | Rating (i) Ring Groove 1 | Rating (i) Ring Groove 2 | Rating (ii) Demerit | Rating (iii) UC Deposits |
|---|---|---|---|---|
| Oil 1 | 6.25 | 0.00 | 381 | 25.90 |
| Reference Oil 1 | 37.25 | 15.75 | 1,433 | 74.10 |
| Reference Oil 1 | 4.25 | 5.00 | 1,066 | 67.40 |
| Oil 2 | 0.00 | 0.50 | 527 | 21.60 |
| Reference Oil 3 | 8.00 | 2.50 | 1,198 | 46.80 |

For each rating, lower values represent a superior performance. The results show that, for the compositions of TBN 30, the composition of the invention (Oil 1) is better in almost all tests than the comparison compositions (Reference Oils 1 and 2). They also show that, for compositions of TBN 40, the composition of the invention (Oil 2) is better in all tests than the comparison composition (Reference Oil 3).

The invention claimed is:

1. A method of lubricating a four stroke medium speed compression-ignited marine engine, which method comprises supplying to the engine crankcase a trunk piston engine oil lubricating composition comprising:
   (A) an oil of lubricating viscosity, in a major amount:
   (B) an oil-soluble overbased metal detergent additive, as the sole overbased metal detergent, consisting of one or more aromatic carboxylates, in a minor amount; and
   (C) an antiwear additive, in a minor amount;
   wherein said lubricating oil composition is dispersant-free and has a Total Base Number (TBN) of 25 or greater.

2. The method as claimed in claim 1, wherein said lubricating oil composition further comprises a fuel oil with a residual fuel content, in a minor amount.

3. The method as claimed in claim 1, wherein said lubricating oil composition has a TBN in the range of 25 to 100.

4. The method as claimed claim 1, wherein component (B) is present in the composition in an amount in the range of 0.5 to 30 mass %.

5. The method as claimed in claim 1, wherein the one or more overbased metal detergent has or have a TBN in the range of 60 to 600.

6. The method as claimed in claim 1, wherein the one or more overbased metal detergent is or are calcium salicylates.

7. The method as claimed in claim 1, wherein the antiwear additive is a zinc salt.

8. A method of lubricating a four-stroke medium speed compression-ignited marine engine, which method comprises supplying to the engine crankcase a trunk piston engine oil lubricating composition comprising:
   (A) an oil of lubricating viscosity, in a major amount;
   (B) an oil-soluble overbased metal detergent additive consisting of, as the sole overbased metal detergent, one or more hydrocarbyl-substituted salicylates, in a minor amount; and
   (C) an antiwear additive comprising a dihydrocarbyl dithiophohate metal salt, in a minor amount;
   wherein said lubricating oil composition is dispersant-free and has a Total Base Number (TBN) of 25 or greater.

9. The method as claimed in claim 8, wherein said lubricating oil composition further comprises a fuel oil with a residual fuel content, in a minor amount.

10. The method as claimed in claim 8, wherein said lubricating oil composition has a TBN in the range of 25 to 100.

11. The method as claimed in claim 8, wherein component (B) is present in the composition in an amount in the range of 0.5 to 30 mass %.

12. The method as claimed in claim 8, wherein the one or more overbased metal detergent has or have a TBN in the range of 60 to 600.

13. The method as claimed in claim 8, wherein the one or more overbased metal detergent is or are calcium salicylates.

14. The method as claimed in claim 8, wherein the antiwear additive is a zinc salt.

* * * * *

UNITED STATES PATENT AND TRADEMARK OFFICE
CERTIFICATE OF CORRECTION

PATENT NO. : 7,053,027 B2
APPLICATION NO. : 09/846483
DATED : May 30, 2006
INVENTOR(S) : Laurent Chambard and Terence Garner Page 1 of 1

It is certified that error appears in the above-identified patent and that said Letters Patent is hereby corrected as shown below:

In claim 8, column 8, line 38, delete "dithiophohate" and insert -- dithiophosphate--.

Signed and Sealed this

Fifteenth Day of August, 2006

JON W. DUDAS
*Director of the United States Patent and Trademark Office*